United States Patent [19]
Sabourin

[11] Patent Number: 5,455,358
[45] Date of Patent: Oct. 3, 1995

[54] FUEL COMPOSITIONS CONTAINING ALKYL-SUBSTITUTED CYCLIC UREA-SUBSTITUTED AMINES

[75] Inventor: Edward T. Sabourin, Novato, Calif.

[73] Assignee: Chevron U.S.A. Inc., San Francisco, Calif.

[21] Appl. No.: 194,138

[22] Filed: Feb. 9, 1994

Related U.S. Application Data

[63] Continuation of Ser. No. 833,545, Feb. 10, 1992, abandoned.

[51] Int. Cl.$^6$ ............ C07D 233/36; C07D 239/10
[52] U.S. Cl. ............ 548/324.5; 544/316
[58] Field of Search ............ 548/324.5; 544/316

[56] References Cited

U.S. PATENT DOCUMENTS

| | | | |
|---|---|---|---|
| 3,380,909 | 4/1968 | Lee | 208/48 |
| 3,438,757 | 4/1969 | Honnen et al. | 44/58 |
| 3,491,025 | 1/1970 | Lee | 252/49.6 |
| 3,556,995 | 1/1971 | Lee et al. | 252/39 |
| 3,565,804 | 2/1971 | Honnen et al. | 252/50 |
| 3,574,576 | 4/1971 | Honnen et al. | 44/72 |
| 3,794,586 | 2/1974 | Kimura et al. | 252/51.5 |
| 3,898,056 | 8/1975 | Honnen | 44/58 |
| 3,960,515 | 6/1976 | Honnen | 44/58 |
| 3,965,084 | 6/1976 | Schiff | 260/96.5 R |
| 4,108,613 | 8/1978 | Frost, Jr. | 44/62 |
| 4,123,232 | 10/1978 | Frost, Jr. | 44/72 |
| 4,191,537 | 3/1980 | Lewis et al. | 44/71 |
| 4,196,090 | 4/1980 | Lilburn | 548/324.5 |
| 4,198,306 | 4/1980 | Lewis | 548/324.5 |
| 4,319,032 | 3/1982 | Sandri et al. | 548/324.5 |
| 4,846,848 | 7/1989 | Miles et al. | 44/62 |

FOREIGN PATENT DOCUMENTS 0622832   6/1961   Canada.

*Primary Examiner*—Jacqueline Haley
*Attorney, Agent, or Firm*—W. K. Turner; E. A. Schaal

[57] ABSTRACT

A fuel composition comprising a major amount of hydrocarbons boiling in the gasoline or diesel range and an effective detergent amount of an alkyl-substituted, five- or six-membered cyclic urea-substituted monoamine or diamine which is the reaction product of:

(a) a halogenated aliphatic hydrocarbon derived from a branched-chain polyolefin having an average molecular weight of about 400 to 5000;

(b) a polyamine having from 3 to 4 amine nitrogen atoms and from 4 to 9 carbon atoms; and thereafter (c) urea.

5 Claims, No Drawings

FUEL COMPOSITIONS CONTAINING ALKYL-SUBSTITUTED CYCLIC UREA-SUBSTITUTED AMINES

This is a continuation of application Ser. No. 07/833,545, filed Feb. 10, 1992, now abandoned.

BACKGROUND OF THE INVENTION

1. Field of the Invention

In recent years, numerous fuel detergents or "deposit control" additives have been developed. These materials when added to hydrocarbon fuels employed in internal combustion engines effectively reduce deposit formation which ordinarily occurs in carburetor ports, throttle bodies, ventures, intake ports and intake valves. The reduction of these deposit levels has resulted in increased engine efficiency and a reduction in the level of hydrocarbon and carbon monoxide emissions.

Furthermore, as engines age, they suffer from a need for a higher octane base gasoline. It is desirable to produce an additive for gasoline which is not only an effective deposit control additive but also has a low ORI (octane requirement increase ) property.

It is, therefore, highly desirable to provide fuel compositions which contain deposit control additives which effectively control deposits in intake systems (carburetor, valves, etc.) of engines operated with fuels containing them and, most preferably, have a low ORI effect.

2. Description of the Prior Art

U.S. Pat. Nos. 3,438,757 and 3,574,576 to Honnen et al. disclose high molecular weight branched-chain aliphatic hydrocarbon N-substituted amines and alkylene polyamines which are useful as detergents and dispersants in hydrocarbonaceous liquid fuels for internal combustion engines. These hydrocarbyl amines and polyamines have molecular weights in the range of about 425 to 10,000, and more usually in the range of about 450 to 5000. Such high molecular weight hydrocarbyl polyamines are also taught to be useful as lubricating oil additives in U.S. Pat. No. 3,565,804 to Honnen et al.

U.S. Pat. Nos. 3,898,056 and 3,960,515 to Honnen et al. disclose a mixture of high and low molecular weight hydrocarbyl amines used as detergents and dispersants at low concentrations in fuels. The high molecular weight hydrocarbyl amine contains at least one hydrocarbyl group having a molecular weight from about 1900 to 5000 and the low molecular weight hydrocarbyl amine contains at least one hydrocarbyl group having a molecular weight from about 300 to 600. The weight ratio of low molecular weight amine to high molecular weight amine in the mixture is maintained between about 0.5:1 and 5:1.

U.S. Pat. Nos. 4,123,232 and 4,108,613 to Frost disclose pour point depressants for hydrocarbonaceous fuels which are the reaction products of an epoxidized alpha olefin containing from 14 to 30 carbon atoms and a nitrogen-containing compound selected from an amine, a polyamine and a hydroxyalkyl amine.

U.S. Pat. No. 3,794,586 to Kimura et al. discloses lubricating oil compositions containing a detergent and antioxidant additive which is a hydroxyalkyl-substituted polyamine prepared by reacting a polyolefin epoxide derived from branched-chain olefins having an average molecular weight of 140 to 3000 with a polyamine selected from alkylene diamines, cycloalkylene diamines, aralkylene diamines, polyalkylene polyamines and aromatic diamines, at a temperature of 15° C. to 180° C.

U.S. Pat. No. 3,380,909 to Lee describes the reaction:

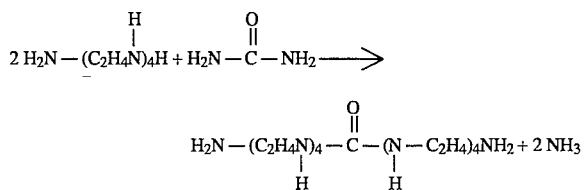

This polyaminourea is reacted with an alkylsuccinimide to make an anti-foulant additive.

The same or similar chemistry is shown in U.S. Pat. Nos. 3,491,025 and 3,556,995 also to Lee and the products are taught as useful as detergents-dispersants in lube oils.

U.S. Pat. No. 3,965,084 to Sidney Schiff entitled "Ashless Dispersant Products and Process" relates to improved additives for lubricants and motor fuels which are prepared by reacting a petroleum sulfonic acid with an adduct formed from an amine and either urea or thiourea (see Col. 1, lines 7 et seq.). A wide variety of amines can be used to form the adduct (see Col. 5, lines 14 to 36), but there is no hydroxyl group on Schiff's adduct. The preferred mole ratio of amine to urea or thiourea is 1.5:1 to 2.25:1 (see Col. 5, lines 38–41). Runs 2 and 3, summarized in Table 1 in Col. 7, show the reaction of tetraethylene pentamine (TEPA) (which is outside the definition of useful amines for the subject invention) with urea and footnote "a" of Table 1 shows that Schiff expected the product to be a dimer. There is no teaching in Schiff that a cyclic urea would be formed. One with ordinary skill in the art would expect (from the teachings of Schiff in Table 1 and in the preferred ratios of amine to urea) the formation of a dimer-like product.

SUMMARY OF THE INVENTION

A fuel composition is provided which contains a deposit control additive which aids the composition in maintaining cleanliness of engine intake systems and has a low ORI factor. Accordingly, the novel fuel composition of the invention comprises a major amount of hydrocarbons boiling in the gasoline or diesel range and an effective detergent amount of an alkyl-substituted, five- or six-membered cyclic urea-substituted monoamine or diamine. These substituted monoamines or diamines are the reaction products of (a) a branched-chain aliphatic hydrocarbon halide having an average molecular weight of about 400 to 5000; (b) a polyamine having from 3 to about 4 amine nitrogen atoms and from 4 to 9 carbon atoms; and (c) urea. The cyclic urea-substituted monoamines or diamines are also new compositions per se.

The present invention further provides a fuel concentrate comprising an inert stable oleophilic organic solvent boiling in the range of from about 150° F. to 400° F. and from 10 to 50 weight percent of the alkyl-substituted, five- or six-membered cyclic urea-substituted monoamine or diamine reaction product described above.

DETAILED DESCRIPTION OF THE INVENTION

The alkyl-substituted, five- or six-membered cyclic urea-substituted monoamine or diamine additive employed in the fuel composition of the present invention comprises the reaction product of (a) a high molecular weight branched-chain aliphatic hydrocarbon halide having an average molecular weight of about 400 to 5000; (b) a polyamine having from 3 to 4 amine nitrogen atoms and from 4 to 9 carbon atoms; and (c) urea. The polyamine component of this reaction product is selected to provide deposit control activity with low octane requirement increase.

The High Molecular Weight Branched-Chain Aliphatic Hydrocarbon Halide Component

The high molecular weight branched-chain aliphatic hydrocarbon halide may have a variety of structures and may be aliphatic or alicyclic, and is generally free of aromatic unsaturation. Preferably the aliphatic hydrocarbon halide is derived from a high molecular weight branched-chain polyolefin having an average molecular weight of about 400 to 5000, preferably from about 900 to 2500. By "halide" in the application is meant chloride or bromide.

Such high molecular weight branched-chain polyolefins are generally mixtures of molecules having different molecular weights and can have at least one branch per 6 carbon atoms along the chain, preferably at least one branch per 4 carbon atoms along the chain, and particularly preferred are those having about one branch per 2 carbon atoms along the chain. These branched-chain olefins may conveniently comprise polyolefins prepared by the polymerization of olefins of from 2 to 6 carbon atoms, and preferably from olefins of from 3 to 4 carbon atoms, and more preferably from propylene or isobutylene. When ethylene is employed, it must be copolymerized with another olefin so as to provide a branched-chain polyolefin. The addition-polymerizable olefins employed are normally 1-olefins. The branch may be of from 1 to 4 carbon atoms, more usually of from 1 to 2 carbon atoms, and preferably methyl.

In general, any high molecular weight branched-chain polyolefin isomer capable of forming a halide and then reacting with a polyamine is suitable for use in preparing the presently employed fuel additives.

Alternatively, various naturally occurring materials may be used which have the desired molecular weight and aliphatic or alicyclic character. These aliphatic hydrocarbons are converted to an aliphatic hydrocarbon halide which then is reacted with the desired amine in the proper mole proportions. The halide is prepared from the hydrocarbon by halogenation: ionically or free radically.

The halogen may be introduced into the hydrocarbon molecule by various means known in the art. Most readily, either chlorine or bromine (halogen of atomic numbers 17 and 35, respectively) may be introduced by the free radical catalyzed halogenation of the hydrocarbon, or ionic addition to olefinic unsaturation. Various free radical catalysts may be used, such as peroxides, azo compounds, bromine, iodine, as well as light. Ionic catalysts are exemplified by ferric chloride. Methods of halogenation are well known in the art and do not require extensive exemplification or illustration here.

The amount of halogen introduced will depend on the particular hydrocarbon used, the desired amount of amine to be introduced into the molecule, the particular alkylene amine used, and the halogen used. The amount of halogen introduced will generally be in the range from about 1 to 5 halogen atoms per molecule, depending on the reactivity of the resulting halide. On a weight percent basis, the amount of halide will generally range from about 1 to 25, more usually from about 1 to 10 weight percent of the branched-chain aliphatic hydrocarbon halide.

Amine Component

The amine component used to prepare the presently employed alkyl-substituted monoamine and diamine reaction products are derived from a polyamine having from 3 to 4 amine nitrogen atoms and from 4 to about 9 carbon atoms. The polyamine is reacted with the branched-chain aliphatic hydrocarbon halide to produce the alkyl-substituted polyamine portion of the fuel additive finding use within the scope of the present invention. The polyamine provides a reaction product; i.e., after reaction of the polyamine with urea, with at least one basic nitrogen atom per product molecule; i.e., a nitrogen atom titratable by a strong acid.

The preferred polyamines finding use within the scope of the present invention are those having the formula:

NH$_2$—Y—NH—X—NH$_2$ where X and Y can be the same or different and are selected from the group consisting of —CH$_2$CH$_2$—; —CH$_2$CH$_2$CH$_2$—; and

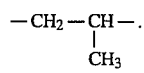

$$-CH_2-CH-.$$
$$\quad\quad\quad\;\; |$$
$$\quad\quad\quad\; CH_3$$

Examples of suitable polyamines include but are not limited to:

(1) diethylenetriamine
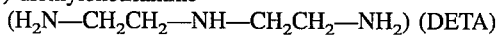
(H$_2$N—CH$_2$CH$_2$—NH—CH$_2$CH$_2$—NH$_2$) (DETA)

(2) di(1,3-propylene)triamine
(H$_2$N—CH$_2$CH$_2$CH$_2$—NH—CH$_2$CH$_2$CH$_2$—NH$_2$)

(3) di(1,2-propylene)triamine

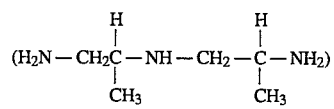

(4) triethylenetetraamine
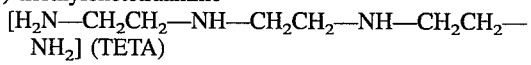
[H$_2$N—CH$_2$CH$_2$—NH—CH$_2$CH$_2$—NH—CH$_2$CH$_2$—NH$_2$] (TETA)

(5) tri(1,3-propylene)tetraamine
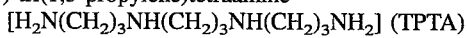
[H$_2$N(CH$_2$)$_3$NH(CH$_2$)$_3$NH(CH$_2$)$_3$NH$_2$] (TPTA)

The halohydrocarbon and alkylene polyamine or polyalkylene polyamine may be brought together neat or in the presence of an inert solvent, particularly a hydrocarbon solvent. The inert hydrocarbon solvent may be aliphatic or aromatic. Also, aliphatic alcohols capable of dissolving the reactants may be used by themselves or in combination with another solvent.

The reaction may be carried out at room temperature (20° C.), but elevated temperatures are preferred. Usually, the temperature will be in the range of from about 100° C. to 225° C. Depending on the temperature of the reaction, the particular halogen used, the mole ratios and the particular amine, as well as the reactant concentrations, the time may vary from 1 to 24 hours, more usually from about 3 to 20 hours. Times greatly in excess of 24 hours do not particularly enhance the yield and may lead to undesirable degradation. It is therefore preferred to limit the reaction time to fewer than 24 hours.

The mole ratio of alkylene amine to halohydrocarbon will generally be in the range from about 0.2 to 10 moles of alkylene amine per mole of halohydrocarbon, more usually 0.5 to 5 moles of alkylene amine per mole of halohydrocarbon. The mole ratio will depend upon the amount of halogen present in the halohydrocarbon, the particular halogen and the desired ratio of amine to hydrocarbon. If complete suppression of polysubstitution of the alkylene polyamines is desired, then large mole excesses of the amine will be used. Thus, the most preferred mole ratio of alkylene amine to halohydrocarbon is in excess of 1:1; generally 3:1 to 5:1.

Small amounts of residual halogen in the final composition are not deleterious. Generally, the residual halogen as bound halogen will be in the range of perhaps 100 ppm to 2 to 5 weight percent of the composition.

Generally, the branched-chain aliphatic portion of the hydrocarbon halide hydrocarbons will have an olefinic double bond. In particular instances, the amines may react in a way resulting in the elimination of hydrogen halide, introducing further aliphatic unsaturation into the hydrocarbon radical. Therefore, the hydrocarbon radicals usually will be olefinically unsaturated. However, the olefinic unsaturation does not significantly affect the utility of the product, and when available, saturated aliphatic halide may be used.

After the reaction has been carried out for a sufficient length of time, the reaction mixture may be extracted with a hydrocarbon medium to free the product from any low molecular weight amine salt which has formed. The product may then be isolated by evaporation of the solvent. Further separation from unreacted hydrocarbon or purification may be carried out as desired, e.g., by chromatography.

Depending on the particular application of the composition of this invention, the reaction may be carried out in the medium in which it will ultimately find use and be formed at concentrations which provide a concentrate of the detergent composition. Thus, the final reaction mixture may be in a form to be used directly upon dilution in fuels.

Urea Component

The third component used in the preparation of the new substituted polyamines of this invention is urea

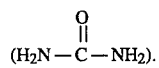

As will be described more fully below, the alkyl-substituted five- or six-membered cyclic urea-substituted monoamines and diamines are prepared by reacting the described halogenated aliphatic hydrocarbon with the defined polyamine and this product is then reacted with urea to form the new cyclic urea compositions of this invention.

The preferred new cyclic ureas are selected from the monoamines and diamines having the formula:

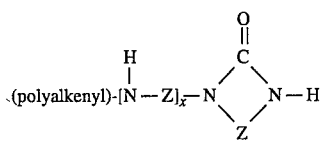

where
polyalkenyl is a branched-chain polyolefin having an average molecular weight from 400 to 5000; preferably from 900 to about 2500 and wherein the olefin has from 2 to 6 carbon atoms, preferably 3 to 4 carbon atoms, and more preferably is propylene or isobutylene;

x is the integer 1 or 2; and

Z is the same or different and is selected from the group consisting of —CH$_2$CH$_2$—; —CH$_2$CH$_2$CH$_2$—; and

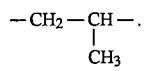

The above formula is an alkyl-substituted five- or six-membered cyclic urea-substituted monoamine when x is 1 or a substituted diamine when x is 2.

Surprisingly, the reaction of the alkyl-substituted monoamine or diamine with urea results in the production of a cyclic urea plus two moles of free ammonia. From the prior art to Lee and Schiff, discussed above, it was expected that a linear dimer of urea would form.

These new cyclic ureas were then found to have surprisingly good detergent and ORI properties as will be shown below.

Preparation Of The Alkyl-Substituted Five- Or Six-Membered Cyclic Urea-Substituted Monoamine Or Diamine Polyamine Reaction Product As noted above, the fuel additive finding use in the present invention is an alkyl-substituted, five- or six-membered cyclic urea-substituted monoamine or diamine which is the reaction product of (a) a halogenated high molecular weight branched-chain aliphatic hydrocarbon, preferably a polyolefin having an average molecular weight of about 400 to 5000; (b) a polyamine having from 3 to 4 amine nitrogen atoms and from 4 to 9 carbon atoms; and (c) urea.

The reaction of (a) with (b) was described above.

The alkyl-substituted polyamine is then reacted with urea and can be represented as follows:

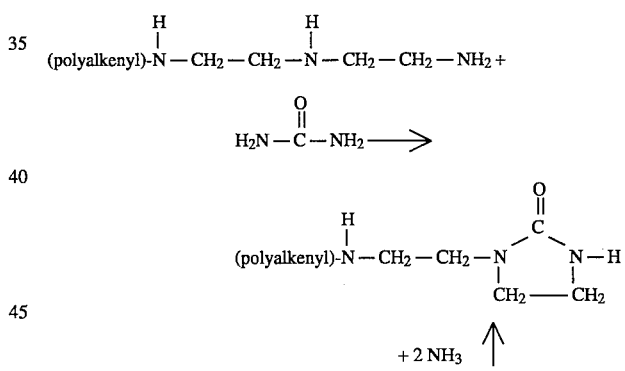

where polyalkenyl is as defined above.

The reaction of the alkyl-substituted polyamine with the urea is usually carried out either neat or with a solvent at a temperature in the range of 75° C. to 250° C., preferably 140° C. to 180° C. The reaction is usually conducted in the absence of oxygen and may be carried out in the presence or absence of a catalyst. The desired product is recovered by sparging with nitrogen or applying a vacuum to remove traces of ammonia. Alternatively a water wash could be used.

The mole ratio of the urea to the alkyl-substituted polyamine is usually about 1:1, but higher or lower ratios can be used. The preferred ratios are 0.8:1 to 1.2:1. The reaction time is usually from 0.5 to 20 hours and more usually from 1 to 8 hours. These reaction variables are not critical and are well within the skill of those in the art.

Ammonia is a gaseous by-product and is usually removed during reaction to drive the reaction to the desired product. The ammonia is removed and treated in known ways.

The reaction solvents, if employed, should be stable and inert to the reactants and products. Preferred solvents include aliphatic or aromatic hydrocarbons or aliphatic alcohols.

Fuel Compositions

The alkyl-substituted, five- or six-membered cyclic urea-substituted monoamine or diamine is useful as an additive for a hydrocarbon distillate fuel. The proper concentration of additive necessary in order to achieve the desired detergency and dispersancy varies depending upon the type of fuel employed, the presence of other detergents, dispersants and other additives, etc. Generally, however, from 30 to 2000 weight ppm, preferably from 100 to 500 ppm of alkyl-substituted monoamine or diamine additives of the invention per part of base fuel is needed to achieve the best results. When other detergents are present, a lesser amount of additive may be used. For performance as a carburetor detergent only, lower concentrations, for example, 30 to 70 ppm may be preferred.

The deposit control additive may be formulated as a concentrate, using an inert stable oleophilic organic solvent boiling in the range of about 150° to 400° F. Preferably, an aliphatic or an aromatic hydrocarbon solvent is used, such as benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the detergent-dispersant additive. In the concentrate, the amount of the additive will be ordinarily at least 10% by weight and generally not exceed 70% by weight, preferably 10–50 weight percent and most preferably from 10 to 25 weight percent.

In gasoline fuels, other fuel additives may also be included such as antiknock agents, e.g., methylcyclopentadienyl manganese tricarbonyl, tetramethyl or tetraethyl lead, or other dispersants or detergents such as various substituted succinimides, amines, etc. Also included may be lead scavengers such as aryl halides, e.g., dichlorobenzene or alkyl halides, e.g., ethylene dibromide. Additionally, antioxidants, metal deactivators and demulsifiers may be present.

A particularly useful additive is a fuel-soluble nonvolatile carrier oil. The carrier fluid employed in this invention is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, synthetic polyoxyalkylene derived oils, and the like, as described, for example, in U.S. Pat. No. 4,191,537 to Lewis. These carrier fluids are believed to act as a carrier for the dispersant and detergent and to assist in removing and retarding deposits.

The carrier fluid employed in the instant invention must also be capable of forming a homogeneous mixture with the other components of the present fuel additive composition. Examples of suitable carrier fluids include Chevron Neutral Oil 500R and Chevron Neutral Oil 600P, available from Chevron U.S.A. Inc., San Francisco, Calif.

Exemplary carrier oils include nonvolatile poly(oxyalkylene) compounds; other synthetic lubricants, i.e., polyalphaolefins or a lubricating mineral oil. The carrier oils are employed in amounts from 100 to 5000 ppm by weight of the fuel, preferably from 500 to 3000 ppm of the fuel. The polyalphaolefins can suitably be those having a viscosity at 100° C. of from 2 to 20 centistokes as more fully described in U.S. Pat. No. 4,846,848 issued Jul. 11, 1989 to R. Miles et al., the description of which is incorporated herein by reference.

EXAMPLES

The following examples are presented to illustrate specific embodiments of the practice of this invention and should not be interpreted as limitations upon the scope of the invention.

Example 1

Chlorination Of Polyisobutylene

A one-liter flask was charged with 400 grams Parapol 1300™ mole weight percent polyisobutylene, purchased from the Paramins of Exxon Chemical Company. The temperature was raised to 90° C. and chlorine was bubbled in slowly for three hours while maintaining the temperature between 90° C. and 100° C. The reaction mixture was thoroughly sparged with nitrogen to remove hydrogen chloride. Analysis indicated the product contained 2.06 weight percent chlorine.

Example 2

Reaction Of Polyisobutenylchloride With Diethylenetriamine (DETA)

A one-liter flask was charged with 302 grams of polyisobutenylchloride from Example 1 and 160 ml diethylenetriamine. The mixture was heated with stirring at 200° C. under a nitrogen atmosphere for 18 hours. The product was cooled to room temperature and dissolved in 800 ml of toluene. The solution was washed twice with 400 ml portions of water/isopropanol (3/1) to remove excess DETA. The solvent (toluene) was removed under vacuum to give 322 grams of product containing 2.45 weight percent nitrogen.

Example 3

Reaction Of Polyisobutenylpolyamine Of Example 2 With Urea

In a 500-ml flask, 201 grams polyisobutenyldiethylenetriamine from Example 2 was mixed with 7 grams of urea and heated to 170° C.–180° C. under a stream of nitrogen to continuously remove by-product ammonia for nine hours with stirring. Vacuum was applied briefly at the end of the reaction to remove any traces of ammonia. The product contained 0.85 weight percent basic nitrogen. Infrared spectroscopy showed a strong absorption at 1702 cm$^{-1}$ indicative of the cyclic urea. The product of 2 moles of the product of Example 2 with urea would have had an infrared spectroscopy absorption at about 1643 cm$^{-1}$ but no absorption at 1643 cm$^{-1}$ was observed.

Intake Valve Deposit Control Evaluation

A test was performed wherein the alkyl-substituted, cyclic urea-substituted amine of Example 3 was blended in gasoline and the deposit control capacity tested in an ASTM/CFR Single-Cylinder Engine Test.

In carrying out the test, a Waukesha CFR single-cylinder engine was used, labelled "12B" in Table 1 below. The run was carried out for 15 hours, at the end of which time the intake valve is removed, washed with hexane and weighed. The previously determined weight of the clean valve is subtracted from the weight of the valve. The difference between the two weights is the weight of the deposit with a lesser amount of deposit measured connoting a superior additive. The operating conditions of the test are as follows: water jacket temperature 100° C. (212° F.); manifold vacuum of 12 in. Hg; intake mixture temperature 50.2° C. (125° F.); air-fuel ratio of 12; ignition spark timing of 40°BTC; engine speed is 1800 rpm; the crankcase oil is a commercial 30 W oil. The amount of carbonaceous deposit in milligrams on the intake valves is measured and reported in the following Table 1.

The base fuel tested in the above test is a regular octane unleaded gasoline containing no fuel deposit control additive. The base fuel is admixed with the additive of Example 3 at 200 ppma (parts per million of actives). Also presented in Table 1 for comparison purposes are values for (i) a commercially available polybutene amine deposit control additive and (ii) a commercially available polyether amine deposit control additive, each having recognized performance in the field.

TABLE 1

| EX. NO. | ADDITIVE | PPMA[6] | PPM 500R[7] | SITV[1], mg | ORI | CCD[5], gm |
|---|---|---|---|---|---|---|
| 4 | None | — | — | 253.1 | 1.8 | 1.16 |
| 5 | CA1[2] | 200 | 800 | 0.84; 1.4 | 5.2; 5.1 | 2.09; 2.27 |
| 6 | CA2[3] | 200 | — | 20.3; 16.1 | 3.1; 3.1 | 1.39; 1.40 |
| 7 | Ex. 3 | 200[4] | — | 14.5; 11.9 | 4.6 | 1.89 |

[1]SCITV = Single Cylinder Intake Valve.
[2]CA1 = Commercial Additive 1 (a polybutene amine).
[3]CA2 = Commercial 2 (a polyether amine).
[4]More than one number indicates more than one test.
[5]CCD = Combustion Chamber Deposits.
[6]PPMA = Parts per million actives.
[7]500R = A mineral oil carrier oil available from Chevron U.S.A. Chevron Neutral Oil 500R is a highly refined based oil having a pour point of −12° C. (Max.) and a viscosity of 98.6 cSt at 40° C.

Comparing Example 7 in Table 1 with Examples 4 through 6 shows that the additive of this invention results in a substantial decrease in SCITV deposits over the base gasoline (Example 4) and is comparable with commercially available deposit control additives (compare Example 7 with Examples 5 and 6).

Again, comparing the ORI performance of the additives of this invention (Example 7) with the base fuel (Example 4) and commercially available additives (Examples 5 and 6), shows the additives of this invention give results which are comparable to the commercial additives.

What is claimed is:

1. A cyclic urea having the formula:

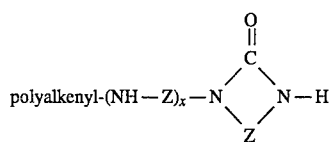

wherein
the polyalkenyl group has an average molecular weight from 400 to 5000 and is branched with at least one branch per six carbon atoms along the chain;
x is the integer 1 or 2; and
Z is the same or different and is selected from the group consisting of —$CH_2CH_2$—; —$CH_2CH_2CH_2$—; and

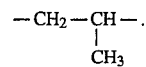

2. A cyclic urea in accordance with claim 1 wherein said polyalkenyl group has an average molecular weight from about 900 to 2500.

3. A cyclic urea in accordance with claim 1 where Z is selected from —$CH_2CH_2$— and

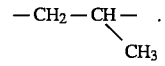

4. A cyclic urea in accordance to claim 1 prepared by the reaction of (i) a halogenated branched-chain aliphatic hydrocarbon having an average molecular weight of about 400 to 5000, and is branched with at least one branch per six carbon atoms along the chain, (ii) a polyamine having from 3 to 4 amine nitrogen atoms and from 4 to about 9 carbon atoms and (iii) urea.

5. A cyclic urea in accordance with claim 4 wherein said aliphatic hydrocarbon has an average molecular weight from about 900 to 2500; and wherein said halogenated branched-chain aliphatic hydrocarbon is branched with from 3 to 4 carbon atoms along the chain.

* * * * *